United States Patent [19]

Effland et al.

[11] Patent Number: 5,015,637
[45] Date of Patent: May 14, 1991

[54] PYRIDO[3,4-B]PYRROLO[1,2-E][1,4,5]OX-ADIAZEPINES

[75] Inventors: Richard C. Effland, Bridgewater; Larry Davis, Sergeantsville, both of N.J.

[73] Assignee: Hoechst-Roussel Pharmaceutical Inc., Somerville, N.J.

[21] Appl. No.: 529,082

[22] Filed: May 25, 1990

[51] Int. Cl.$^5$ .................... C07D 273/06; A61K 31/55
[52] U.S. Cl. .................... 514/211; 540/545; 540/548
[58] Field of Search .................... 540/545; 514/211

[56] References Cited

U.S. PATENT DOCUMENTS 4,450,108  5/1984  Fischer et al. .................... 260/243.3
4,879,382  11/1989  Effland et al. .................... 540/554

OTHER PUBLICATIONS

Stefancich et al., *Synthesis*, (1983), pp. 757-759.

Primary Examiner—Mukund J. Shah
Assistant Examiner—Philip F. Datlow
Attorney, Agent, or Firm—Tatsuya Ikeda

[57] ABSTRACT

There are disclosed various compounds of the formula below,

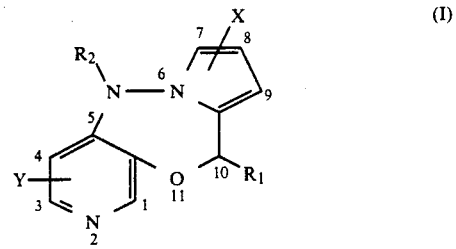

where
 X is hydrogen, halogen or loweralkyl;
 Y is hydrogen, halogen, loweralkyl, loweralkoxy or trifluoromethyl;
 $R_1$ is hydrogen, loweralkyl, aryl, arylloweralkyl, diloweralkylaminoloweralkyl or

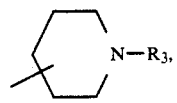

$R_3$ being hydrogen, loweralkyl or arylloweralkyl; and
 $R_2$ is hydrogen, loweralkyl or arylloweralkyl;
which compounds are useful as analgesic agents.

9 Claims, No Drawings

PYRIDO[3,4-B]PYRROLO[1,2-E][1,4,5]OXADIAZE-PINES

The present invention relates to compounds of the formula,

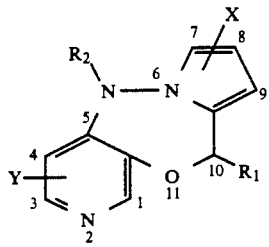

where
X is hydrogen, halogen or loweralkyl;
Y is hydrogen, halogen, loweralkyl, loweralkoxy or trifluoromethyl;
$R_1$ is hydrogen, loweralkyl, aryl, arylloweralkyl, diloweralkylaminoloweralkyl or

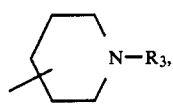

$R_3$ being hydrogen, loweralkyl or arylloweralkyl; and
$R_2$ is hydrogen, loweralkyl or arylloweralkyl;
which compounds are useful as analgesic agents.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term halogen shall mean fluorine, chlorine, bromine or iodine.

The term aryl in each occurrence shall mean an unsubstituted phenyl group or a phenyl group substituted with 1, 2 or 3 substituent groups each of which being independently loweralkyl, halogen, nitro, loweralkoxy, hydroxy or trifluoromethyl.

The compounds of this invention are prepared by utilizing the synthetic scheme described below.

SYNTHETIC SCHEME

In the description of synthetic steps presented below, the definitions of X, Y, $R_1$, $R_2$ and $R_3$ are as presented above unless as otherwise stated or indicated.

Step A

A compound of Formula II is allowed to react with 4-chloro-3-fluoropyridine to afford a compound of Formula III.

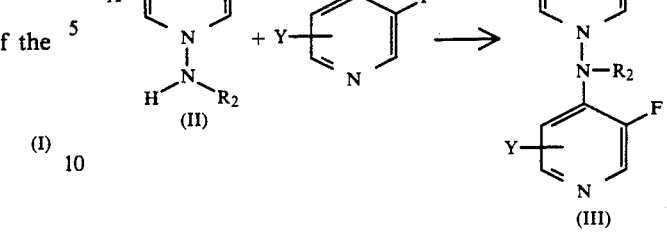

Said reaction is typically conducted in an alcoholic solvents such as methanol, ethanol, isopropanol, etc. or polar aprotic solvent such as dimethylformamide, dimethylacetamide, hexamethylphosphoramide or dimethylsulfoxide at a temperature of between about 20° C. and 150° C.

Step B

Compound III is allowed to react with phosphorus oxychloride and dimethylformamide to afford a compound of Formula IV.

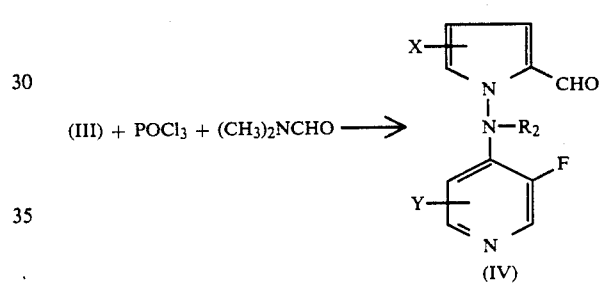

Said reaction can be conducted under conditions usually used for carrying out Vilsmeier reactions. Typically, it is conducted in a suitable solvent such as halogenated hydrocarbon at a temperature of about 20°–100° C.

Step C

Compound IV is reduced with sodium borohydride in a routine manner known to the art to afford a compound of Formula V.

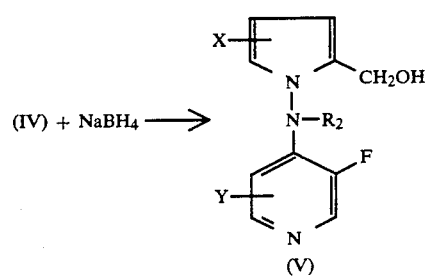

Step D

Compound IV is allowed to react with a Grignard reagent of the formula $R_1$-Mg-Hal where Hal is chlorine or bromine in a routine manner known to the art to afford a compound of the Formula VI.

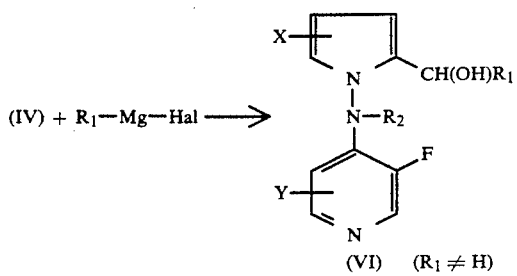

Step E

Compound V or VI is allowed to cyclize with the aid of a strong base such as sodium hydride to afford Compound I. Typically, this reaction is conducted in a suitable solvent such as dimethylformamide at a temperature of about 25° to 130° C.

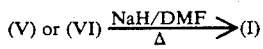

Compounds I of the present invention are also useful as analgesic agents due to their ability to alleviate pain in mammals. The activity of the compound is demonstrated in the 2-phenyl-1,4-benzoquinone-induced writhing (PQW) test in mice, a standard assay for analgesics [Proc. Soc. Exptl. Biol. Med., 95, 729 (1957)].

Inhibition of Phenylquinone-Induced Writhing in Mice (PQW)

A 0.125% concentration of phenyl-p-benzoquinone in a 5% aqueous solution of ethyl alcohol is administered to mice (10 mL/kg, ip). This produces a characteristic "writhe" which is defined as an inward rotation of one or more feet with twisting and turning of the trunk, drawing in of the abdominal wall, lordosis, and arching of the back. A total of 28 male CD-1 Charles River mice (18–30 g) are employed for a time-response. Animals receive food and water ad libitum during their stay in the animal quarters prior to testing. Compounds are tested at 20 mg/kg, sc and are prepared with distilled water, and if insoluble one drop of Tween-80, a surfactant, is added. Compounds are administered in a dosage volume of 10 mL/kg.

Twenty mice (five per group) are administered the test compound at various pretreat time (e.g., 15, 30, 45, and 60 min) prior to phenylquinone injection. Control animals (two per group) receive an equal volume of vehicle. After the administration of phenylquinone, the mice are placed separately into 1-L beakers, and 5 min are allowed to elapse. The mice are then observed for a period of 10 min, and the number of writhes is recorded for each animal. The formula for computing percent inhibition is $$\frac{(\overline{X} \text{ writhes in control group}) - (\overline{X} \text{ writhes in drug group})}{\overline{X} \text{ writhes in control group}} \times 100\%$$

The time period with the maximum percent of inhibition is considered the peak time. A dose-response is reserved for interesting compounds or those which inhibit writhing by 70% or more. A dose-response is run in the same manner as a time-response except 10 animals per group are tested at the peak time of drug activity. Fifty animals, divided among four drug groups and one vehicle control group, are employed. The mice are normally given four doses of drug, each twice the amount of the preceding dose. An $ED_{50}$ is calculated by a computer linear regression analysis.

Results of this assay for some of the compounds of this invention and a reference compound are shown in Table 1.

TABLE 1

| Compound | % Inhibition of Writhing @ 20 mg/kg, s.c. |
|---|---|
| 5-Methyl-5H,10H-pyrido[3,4-b]-pyrrolo[1,2-e][1,4,5]-oxadiazepine | 58% |
| 5-Methyl-10-(1-methyl-4-piperidinyl)-5H,10H-pyrido[3,4-b]pyrrolo[1,2-e]-[1,4,5]oxadiazepine. | 47% |
| Pentazocine | 50%* |

*at the dose of 1.3 mg/kg, s.c.

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of the invention include:
5H,10H-pyrido[3,4-b]pyrrolo[1,2-e][1,4,5]oxadiazepine;
5-Methyl-5H,10H-pyrido[3,4-b]pyrrolo[1,2-e][1,4,5]oxadiazepine;
5-Methyl-10-(1-methyl-4-piperidinyl)-5H,10H-pyrido[3,4-b]pyrrolo[1,2-e][1,4,5]oxadiazepine;
5-Methyl-10-(4-piperidinyl)-5H,10H-pyrido[3,4-b]pyrrolo[1,2-e][1,4,5]oxadiazepine;
5-Methyl-10-(1-benzyl-4-piperidinyl)-5H,10H-pyrido[3,4-b]pyrrolo[1,2-e][1,4,5]oxadiazepine;
5-Methyl-10-(1-phenylethyl-4-piperidinyl)-5H,10H-pyrido[3,4-b]pyrrolo[1,2-e][1,4,5]oxadiazepine;
5-Methyl-10-(N,N-dimethylaminopropyl)-5H,10H-pyrido[3,4-b]pyrrolo[1,2-e][1,4,5]oxadiazepine; and
5-Methyl-10-phenyl-5H,10H-pyrido[3,4-b]pyrrolo[1,2-e][1,4,5]oxadiazepine.

The following examples are presented in order to illustrate this invention.

EXAMPLE 1

N-(3-Fluoro-4-pyridinyl)-N-methyl-1H-pyrrol-1-amine

To 25 ml isopropanol were sequentially added 4-chloro-3-fluoropyridine (4.0 g), a few drops of ethereal HCl and a solution of N-methylaminopyrrolo (3.0 g) in 20 ml of isopropanol.

The mixture was stirred at reflux (100° C.) for four hours, poured into 100 ml of water and stirred for a few minutes. The pH was adjusted to 10 with $Na_2CO_3$, and the mixture was extracted with ether (2×). The ether solution was washed with water and dried (saturated NaCl, anhydrous $MgSO_4$).

After filtration, the solvent was removed by evaporation to afford 7 g of an oil which was eluted on a silica gel column with 10% ethyl acetate/dichloromethane via HPLC (high pressure liquid chromatography). The desired fractions were combined and concentrated to a thick oil (2.6 g), which was dissolved in ether and acidified to pH 1 with ethereal maleic acid. The resultant precipitate was collected and dried to give 3.5 g of product, m.p. 155°–158° C. (dec.). This material was recrystallized from ethanol/ether (1:10) to give 2.3 g of product, m.p. 157°–158° C. (dec.).

ANALYSIS: Calculated for $C_{10}H_{10}FN_3 \cdot C_4H_4O_4$: 54.72% C; 4.59% H; 13.68% N. Found: 54.65% C; 4.58% H; 13.62% N.

EXAMPLE 2

1-(3-Fluoro-4-pyridinylmethylamino)-1H-pyrrol-2-carboxaldehyde

To 14 ml of cold dimethylformamide was added phosphorus oxychloride (18 ml) dropwise in fifteen minutes. The resultant paste was stirred at ambient temperature for ten minutes, and thereafter a solution of N-(3-fluoro-4-pyridinyl)-N-methyl-1H-pyrrol-1-amine (15.8 g) in 100 ml dichloroethane was added.

After stirring at 90° C. for two hours, the mixture was poured into a solution of $NaOCOCH_3 \cdot 3H_2O$ (50 g) in 150 ml of water. After stirring for five minutes, the pH was adjusted to 8 with $Na_2CO_3$, and the mixture was extracted with ethyl acetate (3×). The organic layer was washed with water (2×) and dried (saturated NaCl, anhydrous $MgSO_4$).

After filtration, the solvents were removed by evaporation to leave behind 16 g of an oil, which was eluted on a silica gel column with ethyl acetate via HPLC. The desired fractions were combined and concentrated to a thick oil, which solidified on cooling to a solid, 12.8 g, m.p. 69°–70°.

ANALYSIS: Calculated for $C_{11}H_{10}FN_3O$: 60.27% C; 4.60% H; 19.17% N. Found: 60.08% C; 4.59% H; 19.12% N.

EXAMPLE 3

1-(3-Fluoro-4-pyridinylmethylamino)-1H-pyrrol-2-methanol

To a cold solution of 1-(3-fluoro-4-pyridinylmethylamino)-1H-pyrrol-2-carboxaldehyde (5.0 g) in 100 ml of ethanol, was added $NaBH_4$ (2.0 g). After stirring at 5° C. for one hour, and then at ambient temperature for an additional hour, the mixture was concentrated to an oil, which was stirred with 100 ml of water for five minutes and extracted with ethyl acetate. The organic layer was washed with water and dried (saturated NaCl, anhydrous $MgSO_4$).

After filtration, the solvent was removed by evaporation to leave behind an oil; which was eluted on a silica gel column with ethyl acetate via HPLC. The desired fractions were combined and concentrated to an oil, which solidified on standing to afford 4.0 g of product, m.p. 84°–86° C.

ANALYSIS: Calculated for $C_{11}H_{12}FN_3O$: 59.72% C; 5.47% H; 18.99% N. Found: 59.92% C; 5.51% H; 18.87% N.

EXAMPLE 4

5-Methyl-5H,10H-pyrido[3,4-b]pyrrolo[1,2-e][1,4,5]-oxadiazepine

To a solution of 1-(3-fluoro-4-pyridinylmethylamino)-1H-pyrrol-2-methanol (4.4 g) in 75 ml of dimethylformamide (DMF) was added NaH (0.92 g).

After stirring at 80° C. for two hours, the mixture was cooled, poured into 200 ml of iced-water, stirred for five minutes, and extracted with ethyl acetate. The organic layer was washed with water and dried (saturated NaCl, anhydrous $MgSO_4$).

After filtration, the solvent was removed by evaporation to leave behind a solid (4.0 g), m.p. 130° C., which was eluted on a silica gel column with ethyl acetate via HPLC. The desired fraction was concentrated to a solid 3.0 g (m.p. 138°-139° C.), which was recrystallized from ether/hexanes (1:1) to give crystals, 2.3 g, m.p. 138°-139° C.

ANALYSIS: Calculated for $C_{11}H_{11}N_3O$: 65.65% C; 5.51% H; 20.88% N. Found: 65.53% C; 5.52% H; 20.88% N.

EXAMPLE 5

[1-(3-Fluoro-4-pyridinylmethylamino)-α-(1-methyl-4-piperidinyl)]-1H-pyrrol-2-methanol To a suspension of magnesium turnings (1.7 g) in 25 ml of tetrahydrofuran was added a solution of 4-chloro-1-methylpiperidine (9.5 g) in 30 ml of tetrahydrofuran. (The reaction was initiated with a few drops of dibromoethane and heat). After stirring at reflux for one hour, the mixture was cooled, and thereafter a solution of 1-(3-fluoro-4-pyridinylmethylamino)-1H-pyrrol-2-carboxaldehyde (7.3 g) in 50 ml of tetrahydrofuran was added with vigorous stirring.

After stirring at ambient temperature for an additional hour, the mixture was poured into an ice-cold NH$_4$Cl solution, stirred for five minutes, and extracted with ethyl acetate (3×). The organic layer was washed with water (2×) and dried (saturated NaCl, anhydrous MgSO$_4$).

After filtration, the solvent was removed by evaporation to leave behind a thick oil, 7.0 g, which was eluted on a silica gel column with 50% methanol/dichloromethane via HPLC. The desired fractions were combined and concentrated to a solid, 4.0 g, m.p. 138°-140° C. This material was recrystallized from hexanes/ether (1:1) to give a solid, 3.5 g, m.p. 147°-148° C.

ANALYSIS: Calculated for $C_{17}H_{23}FN_4O$: 64.13% C; 7.28% H; 17.60% N. Found: 63.83% C; 7.25% H; 17.27% N.

EXAMPLE 6

5-Methyl-10-(1-methyl-4-piperidinyl)-5H,10H-pyrido[3,4-b]pyrrolo[1,2-e][1,4,5]oxadiazepine To a suspension of NaH (1.0 g) in 25 ml of dimethylformamide, was added a solution of [1-(3-fluoro-4-pyridinylmethylamino)-α-(1-methyl-4-piperidinyl)]-1H-pyrrol-2-methanol (6.0 g) in 80 ml of dimethylformamide.

After stirring at 80° C. for ten hours, the mixture was cooled, poured into 200 ml of ice-water, stirred for five minutes, and extracted with ethyl acetate. The organic layer was washed with water (2×) and dried (saturated NaCl, anhydrous MgSO$_4$).

After filtration, the solvent was removed by evaporation to leave behind an oil, 5.2 g, which was eluted on a silica gel column with 30% methanol/dichloromethane via HPLC. The desired fractions were combined and concentrated to an oil (2.6 g), which was eluted on an alumina column with ethyl acetate. The desired fractions were combined and concentrated to a oil, 2.1 g, which solidified on standing, m.p. 38°-40° C.

ANALYSIS: Calculated for $C_{17}H_{22}N_4O$: 68.43% C; 7.43% H; 18.78% N. Found: 68.09% C; 7.64% H; 18.36% N.

We claim:

1. A compound of the formula, (I)

where
X is hydrogen, halogen or loweralkyl;
Y is hydrogen, halogen, loweralkyl, loweralkoxy or trifluoromethyl;
R$_1$ is hydrogen, loweralkyl, aryl, arylloweralkyl, diloweralkylaminoloweralkyl or R$_3$ being hydrogen, loweralkyl or arylloweralkyl; and
R$_2$ is hydrogen, loweralkyl or arylloweralkyl;
or a pharmaceutically acceptable acid addition salt thereof.

2. The compound as defined in claim 1, which is 5-methyl-5H,10H-pyrido[3,4-b]pyrrolo[1,2-e][1,4,5]oxadiazepine.

3. The compound as defined in claim 1, which is 5-methyl-10-(1-methyl-4-piperidinyl)-5H,10H-pyrido[3,4-b]pyrrolo[1,2-e][1,4,5]oxadiazepine.

4. The compound as defined in claim 1, which is 5-methyl-10-(4-piperidinyl)-5H,10H-pyrido[3,4-b]pyrrolo[1,2-e][1,4,5]oxadiazepine.

5. The compound as defined in claim 1, which is 5-methyl-10-(1-benzyl-4-piperidinyl)-5H,10H-pyrido[3,4-b]pyrrolo[1,2-e][1,4,5]oxadiazepine.

6. The compound as defined in claim 1, which is 5-methyl-10-(1-phenylethyl-4-piperidinyl)-5H,10H-pyrido[3,4-b]pyrrolo[1,2-e][1,4,5]oxadiazepine.

7. The compound as defined in claim 1, which is 5-methyl-10-(N,N-dimethylaminopropyl)-5H,10H-pyrido[3,4-b]pyrrolo[1,2-e][1,4,5]oxadiazepine.

8. A pharmaceutical composition comprising a compound as defined in claim 1 in an amount effective for alleviating pain in a patient and a suitable carrier therefor.

9. A method of alleviating pain in a patient in need of relief from pain, which comprises administering to such a patient an effective amount of a compound as defined in claim 1.

* * * * *